(12) United States Patent
Lovato

(10) Patent No.: US 9,855,285 B2
(45) Date of Patent: Jan. 2, 2018

(54) METHOD OF INHIBITING THE EXPRESSION OF IL-22 IN ACTIVATED T-CELLS

(71) Applicant: LEO PHARMA A/S, Ballerup (DK)

(72) Inventor: Paola Lovato, Ballerup (DK)

(73) Assignee: LEO PHARMA A/S, Ballerup (DK)

( * ) Notice: Subject to any disclaimer, the term of this patent is extended or adjusted under 35 U.S.C. 154(b) by 87 days.

(21) Appl. No.: 14/648,480

(22) PCT Filed: Nov. 28, 2013

(86) PCT No.: PCT/EP2013/074958
§ 371 (c)(1),
(2) Date: May 29, 2015

(87) PCT Pub. No.: WO2014/083099
PCT Pub. Date: Jun. 5, 2014

(65) Prior Publication Data
US 2015/0297616 A1 Oct. 22, 2015

Related U.S. Application Data

(60) Provisional application No. 61/731,867, filed on Nov. 30, 2012.

(51) Int. Cl.
| | | |
|---|---|---|
| *A61K 31/59* | (2006.01) | |
| *A61K 31/44* | (2006.01) | |
| *A61K 31/4427* | (2006.01) | |
| *A61K 31/593* | (2006.01) | |
| *A61K 45/06* | (2006.01) | |

(52) U.S. Cl.
CPC ............... *A61K 31/59* (2013.01); *A61K 31/44* (2013.01); *A61K 31/4427* (2013.01); *A61K 31/593* (2013.01); *A61K 45/06* (2013.01)

(58) Field of Classification Search
None
See application file for complete search history.

(56) References Cited

FOREIGN PATENT DOCUMENTS

| WO | WO 2006123726 A1 * | 11/2006 | ........... A61K 31/275 |
|---|---|---|---|
| WO | WO 2008/104175 A2 | 9/2008 | |
| WO | WO 2011/076207 A2 | 6/2011 | |

OTHER PUBLICATIONS

Boswell Smith et al., "Selective phosphodiesterase 4 inhibitors in the treatment of allergy and inflammation", Current Opinion in Investigational Drugs, 6 (11), pp. 1136-1141, 2005.
Holden et al., "Monocyte Localization of Elevated cAMP Phosphodiesterase Activity in Atopic Dermatitis", The Society for Investigative Dermatology, Inc., pp. 372-376.
Houslay et al., "Phosphodiesterase-4 as a therapeutic target", Drug Discovery Today, vol. 10, No. 22, pp. 1503-1519, 2005.
Huang et al., "Phosphodiesterase 4 Inhibitors for the Treatment of Asthma and COPD", Current Medicinal Chemistry, 13, pp. 3253-3262, 2006.
Ishii et al., "Antipruritic Effect of the Topical Phosphodiesterase 4 Inhibitor E6005 Ameliorates Skin Lesions in a Mouse Atopic Dermatitis Model", The Journal of Pharamcology and Experimental Therapeutics, 346, pp. 105-112, 2013.
Kroegel et al., "Phosphodiesterase-4 inhibitors as a novel approach for the treatment of respiratory disease: cilomilast", Expert Opinion Investigat. Drugs 16 (1), pp. 109-124, 2007.
McNally et al., "Vitamin D receptor agonists inhibit pro-inflammatory cytokine production from the respiratory epithelium in cystic fibrosis", Journal of cystic fibrosis, Elsevier, NL, 10(6), pp. 428-434, Jun. 28, 2011.
Mitra et al., "Topical delivery for the treatment of psoriasis", Expert delivery on drug delivery, Informa Healthcare, GB, 7(8), pp. 977-992, Aug. 1, 2010.
Press et al., "2 PDE4 Inhibitors—A Review of the Current Field", Progress in Medicinal Chemistry-47, 2009, pp. 37-74.

* cited by examiner

*Primary Examiner* — Michael Barker
(74) *Attorney, Agent, or Firm* — Birch, Stewart, Kolasch & Birch, LLP

(57) ABSTRACT

The present invention relates to a method of inhibiting the upregulation of the expression of the proinflammatory cytokine interleukin-22 (IL-22) in activated and differentiated human T-cells, said upregulation being induced by administration of a therapeutically effective amount of a phosphodiesterase 4 (PDE4) inhibitor. The method comprises administering, either sequentially to or simultaneously with the administration of the PDE4 inhibitor, a vitamin D receptor agonist in an amount sufficient to inhibit the upregulation of IL-22 expression.

8 Claims, 6 Drawing Sheets

METHOD OF INHIBITING THE EXPRESSION OF IL-22 IN ACTIVATED T-CELLS

CROSS REFERENCE TO RELATED APPLICATIONS

This application is the National Phase of PCT International Application No. PCT/EP2013/074958, filed on Nov. 28, 2013, which claims priority under 35 U.S.C. 119(e) to U.S. Provisional Application No. 61/731,867, filed on Nov. 30, 2012, all of which are hereby expressly incorporated by reference into the present application.

FIELD OF INVENTION

The present invention relates to a method of inhibiting the expression of interleukin-22 in activated and differentiated human T-cells as well as a pharmaceutical composition for use in the method.

BACKGROUND OF THE INVENTION

Phosphodiesterases are enzymes that catalyse the hydrolysis of cyclic AMP and/or cyclic GMP in cells to 5-AMP and 5-GMP, respectively, and as such they are critical to cellular regulation of cAMP or cGMP levels. Of the 11 phosphodiesterases identified so far, phosphodiesterase (PDE) 4, PDE7 and PDE8 are selective for cAMP. PDE4 is the most important modulator of cAMP expressed in immune and inflammatory cells such as neutrophils, macrophages and T-lymphocytes (Z. Huang and J. A. Mancini, *Current Med. Chem.* 13, 2006, pp. 3253-3262). As cAMP is a key second messenger in the modulation of inflammatory responses, PDE4 has been found to regulate inflammatory responses of inflammatory cells by modulating proinflammatory cytokines such as TNFα, IL-2, IFN-γ, GM-CSF and LTB4. Inhibition of PDE4 has therefore become an attractive target for the therapy of inflammatory diseases such as asthma, chronic obstructive pulmonary disease (COPD), rheumatoid arthritis, atopic dermatitis, Crohn's disease etc. (M. D. Houslay et al., *Drug Discovery Today* 10 (22), 2005, pp. 1503-1519; N. Press & K. H. Banner, *Progress in Medicinal Chemistry* 47, 2009, pp. 37-74). As atopic dermatitis (AD) patients have increased PDE-activity, PDE4-inhibition would also appear to be a viable treatment of AD (Journal of Investigative Dermatology (1986), 87(3), 372-6; N. Ishii et al., *J. Pharmacol. Exper. Ter.* 346, 2013, pp. 105-112).

The PDE4 gene family consists at least of four genes, A, B, C and D, which have a high degree of homology (V. Boswell Smith and D. Spina, *Curr. Opinion Investig. Drugs* 6(11), 2006, pp. 1136-1141). The four PDE4 isoforms are differentially expressed in different tissues and cell types. Thus, PDE4B is predominantly expressed in monocytes and neutrophils, but not in cortex and epithelial cells, while PDE4D is expressed in lung, cortex, cerebellum and T-cells (C. Kroegel and M. Foerster, *Exp. Opinion Investig. Drugs* 16(1), 2007, pp. 109-124).

Numerous PDE4 inhibitors have been studied for their therapeutic effect on inflammatory diseases, primarily asthma, inflammatory bowel disease and COPD. The first of these, theophylline, is a weak, non-selective phosphodiesterase inhibitor used in the treatment of respiratory diseases such as asthma and COPD. Treatment with theophylline may, however, give rise to both mild and severe adverse effects, e.g. arrhythmia and convulsions, restricting the clinical utility of theophylline (Kroegel and Foerster, supra). As phosphodiesterase 4 has remained an attractive target for anti-inflammatory therapy, several other, more selective PDE4 inhibitors have been developed and investigated in a clinical setting. The clinical development of many of the first-generation PDE4 inhibitors such as rolipram was discontinued due to dose-limiting side effects, primarily nausea and emesis. Second-generation PDE4 inhibitors with apparently less pronounced adverse effects are currently in clinical trials (Houslay, supra).

Compounds that exhibit PDE4 inhibitory activity have been proposed as therapeutic agents for systemic treatment of inflammatory allergic diseases such as bronchial asthma, COPD, allergic rhinitis, and nephritis; autoimmune diseases such as rheumatoid arthritis, multiple sclerosis, Crohn's disease, and systemic lupus erythematosus; diseases of the central nervous system such as depression, amnesia, and dementia; organopathy associated with ischemic reflux caused by cardiac failure, shock, and cerebrovascular diseases, and the like; insulin-resistant diabetes; wounds; and other diseases where inflammation plays a part in the etiology or progression of the disease.

Compounds that exhibit PDE4 inhibitory activity may also be beneficial in preventing, treating or ameliorating a variety of dermal diseases or conditions, such as proliferative and inflammatory skin disorders and in particular psoriasis, epidermal inflammation, alopecia, skin atrophy, steroid induced skin atrophy, skin ageing, photo skin ageing, acne, dermatitis, atopic dermatitis, seborrheic dermatitis, contact dermatitis, urticaria, pruritus, and eczema.

One of the pathogenic processes underlying the development of psoriasis is infiltration of the skin by activated immune cells, such as Th1 and Th17 cells, expressing cytokines that induce a self-perpetuating inflammatory cycle in psoriasis plaques. In particular, the cytokines TNFα, IL-17 and IL-22 have been shown to be of pivotal importance to the onset and progression of psoriasis. An in vitro assay using human peripheral blood T-cells that have been activated and differentiated to the Th1/Th17 phenotype was developed to assess the anti-inflammatory effect of test compounds by measuring their effect on cytokine expression.

In the course of research leading to the present invention, it was surprisingly found that when PDE4 inhibitors were tested in the Th1/Th17 assay, they upregulate the expression of the proinflammatory cytokine IL-22 and, to a lesser extent, IL-17. The expression of IL-22 is highly upregulated in patients with psoriasis and atopic dermatitis, stressing its role in chronic skin inflammatory conditions. Through its receptor which is expressed by cells of non-hemapoietic origin, such as epithelial cells including keratinocytes, endothelial cells and fibroblasts, IL-22 plays an important role in the induction of altered proliferation and differentiation of keratinocytes and for the expression of inflammatory molecules such as MCH class I, IL-6 and IL-8, thus promoting skin inflammation. The unexpected upregulation of a proinflammatory cytokine by compounds that have therapeutic potential as anti-inflammatory drugs provides a rationale for concurrent treatment with another therapeutically active compound capable of downregulating the expression of IL-22.

SUMMARY OF THE INVENTION

The vitamin D receptor agonist calcipotriol has been found to be capable of strongly inhibiting the expression of IL-22 in an in vitro assay using activated human T-cells differentiated into Th1/Th17 cells. When calcipotriol was tested together with a series of PDE4 inhibitors in this assay, the upregulation of IL-22 mediated by PDE4 inhibitors was counteracted while the inhibitory effect of PDE4 inhibitors on other proinflammatory cytokines, notably TNFα, was unexpectedly retained.

Accordingly, in one aspect the present invention relates to a method of inhibiting the upregulation of the expression of the proinflammatory cytokine interleukin-22 (IL-22) in activated and differentiated human T-cells, said upregulation being induced by administration of a therapeutically effective amount of a phosphodiesterase 4 (PDE4) inhibitor, the method comprising administering, either sequentially to or simultaneously with the administration of the PDE4 inhibitor, a vitamin D receptor agonist in an amount sufficient to inhibit the upregulation of IL-22 expression.

In another aspect, the invention relates to a pharmaceutical composition for use in the treatment of inflammatory diseases or conditions comprising a therapeutically effective amount of a PDE4 inhibitor and a vitamin D receptor agonist in an amount sufficient to inhibit the upregulation of the expression of the proinflammatory cytokine IL-22 induced by the administration of the PDE4 inhibitor, as well as a pharmaceutically acceptable carrier or vehicle.

DETAILED DESCRIPTION OF THE INVENTION

Definitions

Figure 1:
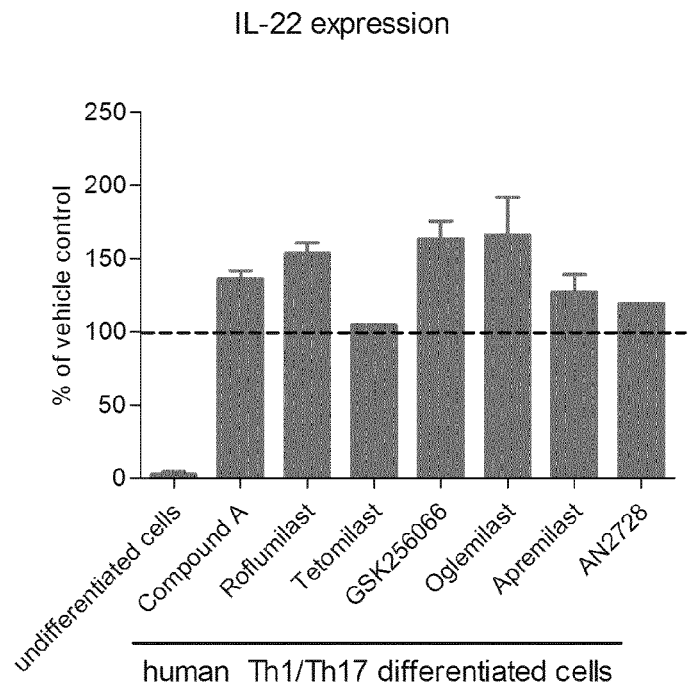
FIG. 1 is a graph showing the upregulation of IL-22 expression in Th1/Th17 cells by seven PDE4 inhibitors in clinical development in a concentration of 1 μM.

In the present context, the term "vitamin D receptor agonist" (or "vitamin D agonist" for short) is intended to indicate a biologically active compound which stimulates the activity of the vitamin D receptor. Vitamin D receptor agonists may be selected from natural vitamin D derivatives or synthetic vitamin D analogues. Calcitriol, calcipotriol, maxacalcitol and tacalcitol are examples of vitamin D receptor agonists that have been found to downregulate the expression of IL-22 in the Th1/Th17 assay disclosed herein (cf. FIG. 6).

"Calcipotriol" is a vitamin D analogue of the formula

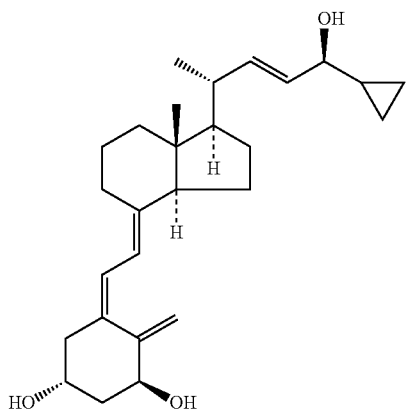

Calcipotriol has been found to exist in two crystalline forms, an anhydrate and a monohydrate. Calcipotriol monohydrate and its preparation are disclosed in WO 94/15912. The term "calcipotriol" is intended to include all forms of the compound.

"Roflumilast" is the compound 3-(cyclopropylmethoxy)-N-(3,5-dichloropyridin-4-yl)4-(difluoromethoxy)benzamide "Tetomilast" is the compound 6-[2-(3,4-diethoxyphenyl)thiazol-4-yl]pyridine-2-caboxylic acid "GSK-256066 is the compound 6-[3-(N,N-dimethylcarbamoyl)phenylsulfonyl]-4-(3-methoxyphenylamino)-8-methylquinoline-3-carboxamide hydrochloride "Oglemilast" is the compound N-(3,5-dichlorpyridin-4-yl)-4-(difluuoromethoxy)-8-methylsulfonylamido)dibenzo(b,d)furan-1-carboxamide "Apremilast" is the compound (+)-N-[2-[1(S)-(3-ethoxy-4-methylphenyl)-2-(methylsulfonyl)ethyl]-1,3-dioxo-2,3-dihydro-1H-isoindol-4-yl]acetamide "AN2728" is the compound 4-(1-hydroxy-1,3-dihydro-2,1-benzoxaborol-5-yloxy)benzonitrile Compound A is the compound 2-{6-[2-(2,3-dichloropyridin-4-yl)acetyl]-2,3-dimethoxyphenoxy}-N-propylacetamide Compound B is the compound N-benzyl-2-{6-[2-(3,5-dichloropyridin-4-yl)acetyl]-2,3-dimethoxyphenoxy}acetamide Compound C is the compound 2-(3,5-dichloropyridin-4-yl)1-{2-[2-(4-fluorophenyl)ethoxy]-3,4-dimethoxyphenyl}ethanone Compound D is the compound 2-(3,5-dichloropyridin-4-yl)-1-{9-methoxy-spiro[2H-1,5-benzodioxepin-3(4H),3'-oxetane]-6-yl}ethanone Compound E is the compound 2-{6-[2-(3,5-dichloropyridin-4-yl)acetyl]-2,3-dimethoxyphenoxy}-N-(2-dimethylaminoethyl)acetamide The term "upregulation of IL-22 expression" is intended to indicate both the upregulation of IL-22 expression in differentiated but untreated T-cells (Th1/Th17 cells) and the further upregulation of the expression of IL-22 in differentiated T-cells treated with a PDE4 inhibitor.

EMBODIMENTS

In psoriatic skin lesions, dendritic cells and T-cells interact with each other and with keratinocytes to link innate and adaptive immune responses via a complex cytokine network which defines psoriasis at the molecular level. Key cytokines produced in psoriatic skin by innate immune cells, in particular inflammatory dendritic cells, are TNFα as well as IL-12 and IL-23, both of which play an important role in the differentiation or expansion of T-cells into Th1 or Th17 cells, respectively. Th1 cells are traditionally characterised by the production of IFN-γ while Th17 cells produce the signature cytokines IL-17, IL-22 and IL-26. The importance of these key mediators in the pathogenesis of psoriasis has been confirmed by their successful targeting with biologics against TNFα, IL-17 and IL-12/IL-23 in the clinic.

Given the major role of the Th17 subset in psoriasis and other chronic immune-mediated inflammatory diseases such as psoriatic arthritis, rheumatic arthritis, multiple sclerosis and inflammatory bowel disease, an in vitro cellular assay was developed using activated human T-cells differentiated into Th1/Th17 cells by a defined cytokine environment that orchestrates the differentiation programme via activation of lineage/phenotype-specific transcription factors factors while concomitantly suppressing factors responsible for the induction of other helper T-cell subsets (see Example 1 below). The resulting Th1/Th17 cells were used to test for the effect of different dosage levels and dosage ratios of the two active ingredients by comparing the expression levels of the proinflammatory cytokines IL-6, IL-8, IL-17, IL-22 and TNF-α resulting from application of different test concentrations individually or together.

In one embodiment, the vitamin D receptor agonist may be selected from the group consisting of calcipotriol, calcitriol, alfacalcidol, tacalcitol, maxacalcitol and paricalcitol. In a currently favoured embodiment for topical application, the vitamin D receptor agonist is calcipotriol or calcipotriol monohydrate.

As the upregulation of IL-22 by PDE4 inhibitors appears to be a class effect, cf. FIG. 1 below, the PDE4 inhibitor may be selected from a wide range of known PDE4 inhibitors such as those selected from the group of roflumilast, GSK256066, oglemilast, tetomilast, apremilast, AN2728, Compound A, Compound B, Compound C, Compound D and Compound E. In a currently favoured embodiment, the PDE4 inhibitor is Compound A (2-{6-[2-(2,3-dichloropyridin-4-yl)acetyl]-2,3-dimethoxyphenoxy}-N-propylacetamide) and Compound D (2-(3,5-dichloropyridin-4-yl)-1-{9-methoxy-spiro[2H-1,5-benzodioxepin-3(4H),3'-oxetane]-6-yl}ethanone).

The present method is suitable for the treatment of an inflammatory disease or condition. In the cellular assay described in Example 1 below, the co-administration of calcipotriol and Compound A has been shown to result in broad cytokine inhibition in Th1/Th17 cells. The inhibition of TNFα and IL-6 by Compound A and the inhibition of IL-22, IL-17 and IL-8 by calcipotriol were maintained by the combination treatment. Most advantageously, the co-administration of calcipotriol resulted in downregulation of the expression of IL-22 mediated by Compound A and other PDE4 inhibitors. It is therefore believed that the co-administration of PDE4 inhibitors and vitamin D receptor agonists may result in a significantly increased anti-inflammatory effect of the PDE4 inhibitor providing an attractive alternative to steroidal treatment. The results presented in FIG. 7 below show that the effect of calcipotriol on IL-22 expression may be obtained at a much lower concentration than that required to affect keratinocyte proliferation. This suggests that the combination of PDE4 inhibitor and vitamin D receptor agonist may be used in the treatment of conditions where an anti-inflammatory effect is needed without concomitantly affecting keratinocyte proliferation.

Examples of inflammatory diseases or conditions that may be treated with a combination of a PDE4 inhibitor and a vitamin D receptor agonist are inflammatory allergic diseases such as bronchial asthma, COPD, allergic rhinitis, and nephritis; autoimmune diseases such as rheumatoid arthritis, multiple sclerosis, Crohn's disease, and systemic lupus erythematosus; organopathy associated with ischemic reflux caused by cardiac failure, shock, and cerebrovascular diseases, and the like; insulin-resistant diabetes; wounds; and other diseases where inflammation plays a part in the etiology or progression of the disease. It is of particular interest to use the present method in the treatment of immune-mediated inflammatory diseases such as psoriasis, psoriatic arthritis, rheumatoid arthritis, multiple sclerosis and inflammatory bowel disease.

In a currently favoured embodiment, the present method may be used in the treatment of an inflammatory skin disease or condition. Examples of inflammatory skin diseases or conditions that may favourably be treated with a combination of a PDE4 inhibitor and a vitamin D receptor agonist are psoriasis, epidermal inflammation, alopecia, skin atrophy, steroid induced skin atrophy, skin ageing, photo skin ageing, acne, dermatitis, atopic dermatitis, seborrheic dermatitis, contact dermatitis, urticaria, pruritus, and eczema. It is of particular interest to use the method in the treatment of inflammatory skin diseases or condition is selected from skin diseases in which upregulation of IL-22 expression plays an important role such as psoriasis or atopic dermatitis.

Based on the results shown in FIG. 7 below, it is currently assumed that concentration of the vitamin D receptor agonist sufficient to inhibit the upregulation of IL-22 expression by the PDE4 inhibitor may be more than 10 times lower than the therapeutically effective concentration of the PDE4 inhibitor. It is currently assumed that the concentration of the vitamin D receptor agonist may be more than 25 times, more than 50 times, more than 100 times, more than 250 times, more than 500 times, more than 750 times, or more than 1000 times lower than the concentration of the PDE4 inhibitor.

Thus, when the concentration of the PDE4 inhibitor in the assay is 1 µM, the concentration of the vitamin D receptor agonist sufficient to inhibit the upregulation of IL-22 expression by the PDE4 inhibitor may be 100 nM or less. The concentration of the vitamin D receptor agonist may conveniently be in the range of 100 nM-100 µM (at a concentration of the PDE4 inhibitor of 1 µM). More specifically, the concentration of the vitamin D receptor agonist may be 75 nM, 50 nM, 40 nM, 30 nM, 25 nM, 20 nM, 10 nM, 5 nM, 1 nM, 0.5 nM or 0.1 nM.

A pharmaceutical composition for use in the present method comprises a therapeutically effective amount of a PDE4 inhibitor and a vitamin D receptor agonist in an amount sufficient to inhibit the upregulation of IL-22 expression induced by the administration of the PDE4 inhibitor as well as a pharmaceutically acceptable carrier or vehicle.

Suitable compositions include e.g. those in a form suitable for oral (including sustained or timed release), transdermal, ophthalmic, topical, dermal, nasal or buccal administration. Topical administration of the claimed composition is particularly suitable when used in the treatment of an inflammatory skin disease or condition.

The compositions may be prepared by any of the methods well known in the art of pharmacy, e.g. as disclosed in Remington, *The Science and Practice of Pharmacy*, 20th ed., 2000. All methods include the step of bringing the active ingredients into association with the carrier, which constitutes one or more excipients. In general, the compositions are prepared by uniformly and intimately bringing the active ingredients into association with a liquid carrier or a finely divided solid carrier or both, and then, if necessary, shaping the product into the desired dosage form.

Compositions of the present invention suitable for oral administration may be in the form of discrete units as capsules, sachets, tablets or lozenges, each containing a predetermined amount of the active ingredients; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose, hydroxypropylmethylcellulose, hydroxypropylcellulose, carbomers and polyvinylpyrrolidone. The active ingredients may also be administered in the form of a bolus, electuary or paste.

A tablet may be made by compressing or moulding the active ingredients with one or more excipients. Compressed tablets may be prepared by compressing, in a suitable machine, the active ingredients in a free-flowing form such as a powder or granules, optionally mixed by a binder, such as e.g. lactose, glucose, starch, gelatine, acacia gum, tragacanth gum, sodium alginate, carboxymethylcellulose, methylcellulose, hydroxypropylmethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredients and suitable carrier moistened with an inert liquid diluent.

For oral administration, the PDE4 inhibitor may be administered in an amount of 0.01-2 mg/kg body weight, more specifically 0.1-1.5 mg/kg body weight or 0.25-1.25 mg/kg body weight or 0.5-1 mg/kg body weight. The amount of the vitamin D agonist should be adjusted accordingly and may be administered in an amount of 0.00001-0.001 mg/kg.

Transdermal compositions may be in the form of a plaster or a patch.

Compositions suitable for ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in Encyclopedia of Pharmaceutical Technology, vol. 2, 1989, may also be used to present the active ingredient for ophthalmic administration.

Compositions suitable for topical or ophthalmic administration include liquid or semi-solid preparations such as liniments, lotions, gels, ointments, aerosols, sprays, films, oil-in-water or water-in-oil emulsions such as creams or pastes; or solutions or suspensions such as drops. Compositions for ophthalmic treatment may preferably additionally contain a cyclodextrin.

For topical administration, the PDE4 inhibitor may typically be present in an amount of from about 0.01 to about 20% by weight of the composition, such as from about 0.1% to about 10% by weight of the composition, but may also be present in an amount of up to about 50% by weight of the composition. The amount of vitamin D receptor agonist should be adjusted accordingly, and the vitamin D receptor agonist may typically be present in the composition in an amount of from about 0.0001 to about 2.0% by weight of the composition.

Compositions suitable for nasal or buccal administration include powder, self-propelling and spray formulations, such as aerosols and atomisers. Such formulations are disclosed in greater detail in e.g. Modern Pharmaceutics, $2^{nd}$ ed., G. S. Banker and C. T. Rhodes (Eds.), page 427-432, Marcel Dekker, New York; Modern Pharmaceutics, $3^{th}$ ed., G. S. Banker and C. T. Rhodes (Eds.), page 618-619 and 718-721, Marcel Dekker, New York and_Encyclopedia of Pharmaceutical Technology, vol. 10, J. Swarbrick and J. C. Boylan (Eds), page 191-221, Marcel Dekker, New York.

In addition to the aforementioned ingredients, the present composition may include one or more additional ingredients such as diluents, buffers, flavouring agents, colourant, surface active agents, thickeners, preservatives, e.g. methyl hydroxybenzoate (including anti-oxidants), emulsifying agents and the like.

EXAMPLES

Example 1

In Vitro Assay Using Activated and Differentiated Human T-Cells to Evaluate the Anti-Inflammatory Effect of Calcipotriol and PDE4 Inhibitors The plasticity of peripheral blood T cells to differentiate into specific T cell subpopulations has been documented in the literature. Therefore, it is anticipated that different lineages of inflammatory T-cell populations can be established by in vitro culture for a limited period of time and used as in vitro cell-based assays, where both the phenotype of inflammatory T cells and the effect of anti-inflammatory drugs may be assessed.

It was of particular interest to develop a protocol for generating human Th1/Th17 cells to test potential new therapies for psoriasis and/or other Th17-related diseases.
Materials and Methods CD4+ T cells were first negatively isolated from human peripheral blood of healthy donors using RosetteSep® separation system from STEMCELL.

Subsequently, CD4+ T cells were activated by crosslinking the cell surface proteins CD3 and CD28 with specific antibodies.

To induce Th1/Th17 differentiation, activated CD4+ T cells were then cultured in flasks at density of $2-5 \times 10^6$ cells per ml of culture in X-VIVO 15 serum-free medium in presence of growth and differentiation factors cocktail, containing the following:
  rhIL-2 at 10 ng/ml
  rhTGF-β at 10 ng/ml
  rhIL-1β at 10 ng/ml
  rhIL-6 at 10 ng/ml
  rhIL-23 at 20 ng/ml
  Antibody anti-IL-4 at 1 µg/ml
  Antibody anti-IL-13 at 1 µg/ml Culture media had been refreshed every second day and T cells were cultured up to 5-7 days to allow a complete differentiation into Th1/Th17 cells.

Once the T cells are differentiated into Th1/Th17 cells, cells are rinsed from the differentiation media and placed in assay media (X-VIVO 15 media containing 10 ng/ml rhIL-2 only) at the final concentration of $1\text{-}1.5\times10^6$ cells/ml in wells with 0.250 ml cell suspension per well ($0.25\text{-}0.375\times10^6$ cells/well/sample) with and without test compound treatment for 24 hours. At the termination time point, the effect of anti-inflammatory drugs is assessed by measuring the level of phenotype related cytokines released in the cell culture supernatants. Duplicates and cells from different donors are used for each treatment.

Results

Characterization of the Th1/Th17 Phenotype Upon In Vitro Culture and Differentiation CD4+ T cells were cultured in vitro up to maximum 7 days. The cellular Th1/Th17 phenotype was evaluated by cytokine analysis of the cell culture supernatant. In particular, after 5-7 days in culture under differentiation pressure, the T cells are rinsed from the differentiation media and placed in basal media at the final concentration of $1\text{-}1.5\times10^6$ cells/ml. The basal media representing the growth media without any differentiation pressure, which is the X-VIVO15 media containing only 2 mM glutamax and 1× pen/strep and 10 ng/ml rhIL-2.

Variation in the Th1/Th17 phenotype was also observed between donors; however, variation is normally minimal while lack of differentiation into Th1/Th17 occurs very rarely (less than 1% of the cases).

Analysis of cytokine expression by differentiated human Th1/Th17 cells showed that the cells are able to well express the Th1 related cytokine IFNγ as well as the Th17 related cytokines IL-17 and IL-22.

Evaluation of the Combination of Calcipotriol and Compound a in the Th1/Th17 Cell Model of Inflammation After differentiation for 5-6 days, all the cells were carefully washed and placed in growth media containing IL-2 (X-VIVO+10 ng/ml IL-2) at a final concentration of $1\text{-}1.5\times10^6$ cells/ml. Dilutions of calcipotriol (12 nM, 100 nM and 120 nM) and Compound A (0.5 µM, 1 µM and 5.6 µM), alone or in combination were added to the full differentiated human Th1/Th17 cells. Assays were performed in duplicates and included undifferentiated human T cells (negative control) and treated or untreated differentiated human Th1/Th17 cells. All cells were cultured under similar conditions in assay media containing 0.1% DMSO with or without test compounds.

Th1/Th17 cells were treated for 24 hours with or without test compounds.

Supernatants were collected from all samples and assessed for cytokine expression (IL-6, IL-8, IL-17, IL-22 and TNF-α). All cytokines were measured (as pg/ml) using MSD kits except IL-22 which was measured by ELISA.

Results

Data analysis and graphs were made in Excel or GraphPad Prism. Statistical analysis was made using 1 way ANOVA corrected by Dunnett's Multiple Comparison Test.

Figure 3A:
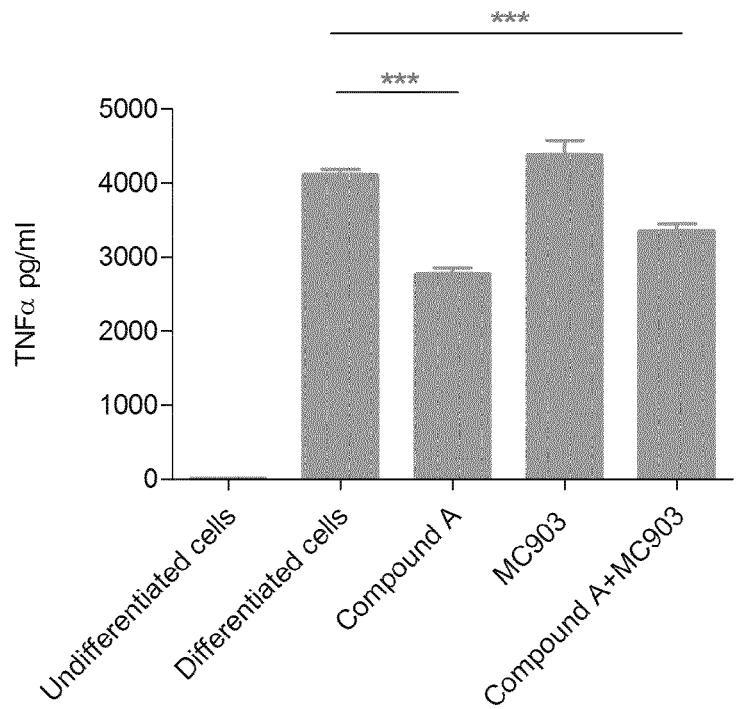
FIG. 3 is a graph showing the effect on the expression of TNFα (FIG. 3a) and IL-22 (FIG. 3b) in Th1/Th17 cells of calcipotriol in a concentration of 120 nM and Compound A in a concentration of 5.6 μM alone and in combination. "MC 903" is calcipotriol.
Figure 3B:
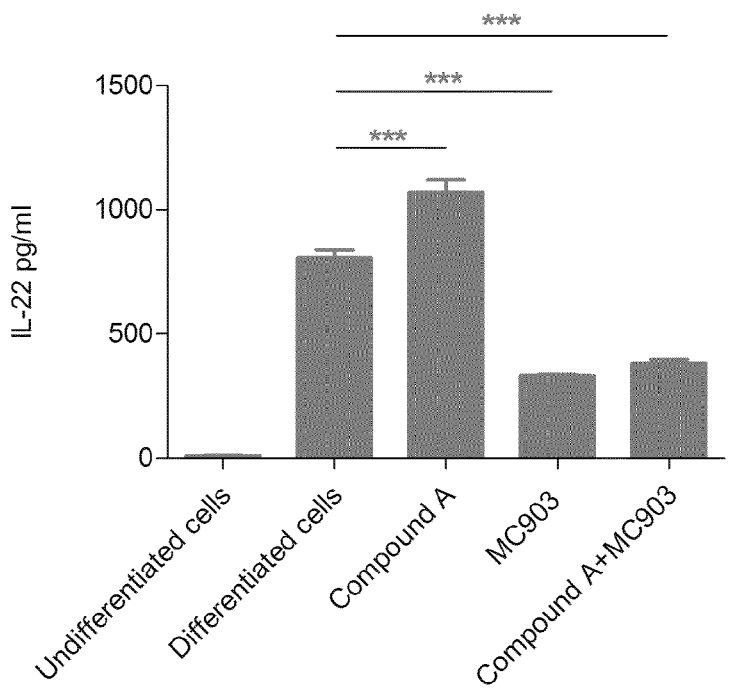

In all the assays performed, calcipotriol alone strongly inhibited the expression of IL-22 (cf. FIG. 3b), IL-8 and, to some extent, IL-17 but did not have any effect on TNFα and IL-6 expression.

Figure 4:
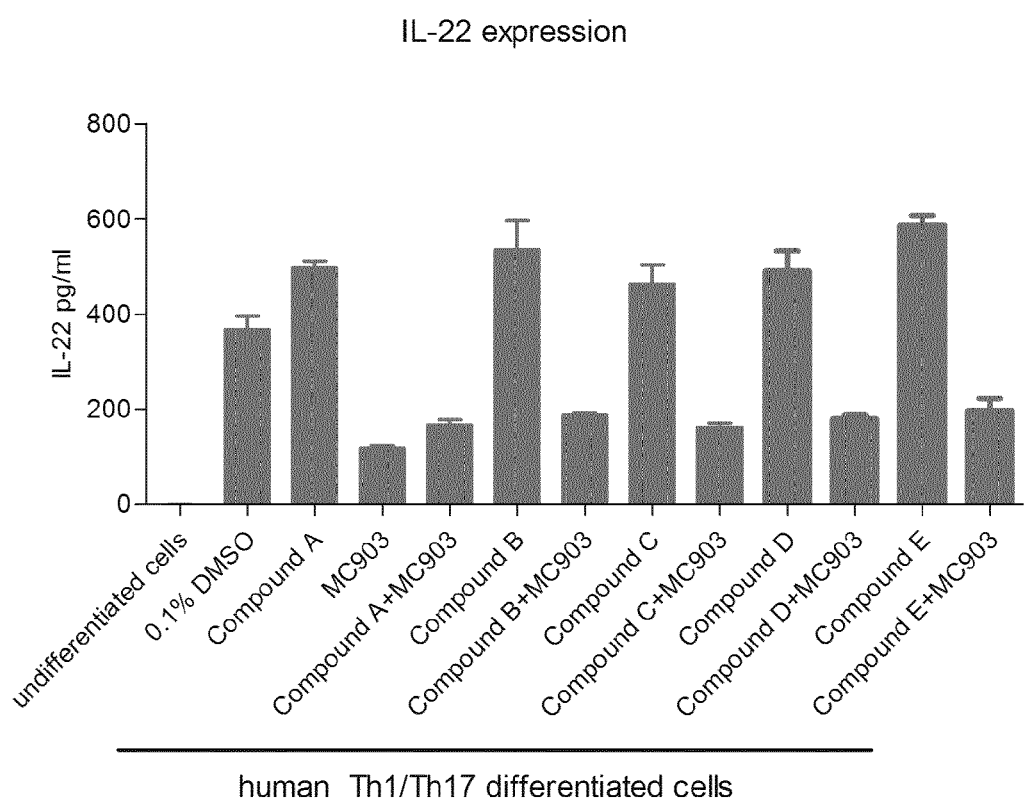
FIG. 4 is a graph showing the effect on the expression of IL-22 in Th1/Th17 cells of calcipotriol in a concentration of 100 nM and five different PDE4 inhibitors in a concentration of 1 μM alone or in combination. "MC 903" is calcipotriol.

Compound A (cf. FIGS. 2 and 3b) and other tested PDE4 inhibitors (cf. FIGS. 1, 4 and 5) alone increased the expression of IL-22 and, to some degree, IL-17, while Compound A strongly decreased the expression of TNFα (cf. FIG. 3a) and weakly of IL-6, but did not have any effect on IL-8.

When calcipotriol and Compound A were coadministered, the combination treatment resulted in broad cytokine inhibition in human Th1/Th17 cells. The inhibition of TNFα and IL-6 by Compound A and the inhibition of IL-22, IL-17, and IL-8 by calcipotriol were maintained by the combination treatment (FIGS. 3a and 3b for TNFα and IL-22, respectively). In these experiments, the ratio of calcipotriol to PDE4 inhibitors was 1:50.

To conclude

Figure 2:
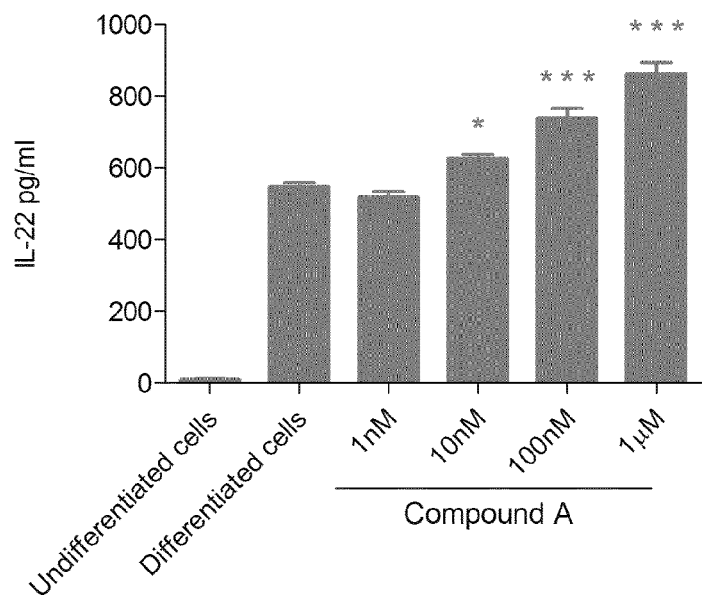
FIG. 2 is a graph showing the dose-dependent upregulation of IL-22 expression in Th1/Th17 cells by Compound A.

Compound A alone significantly inhibits TNFα (FIG. 3a) and IL-6 expression and significantly increases IL-22 expression (FIG. 3b) in human Th1/Th17 cells The capacity to upregulate IL-22 expression is dose-dependent (FIG. 2) and observed with several PDE4 inhibitors (FIG. 1)

Calcipotriol alone significantly inhibits IL-22 expression (FIG. 3b) and inhibits IL-8 and, to some extent, IL-17 expression in human Th1/Th17 cells Combination treatment with calcipotriol and Compound A results in broad cytokine inhibition in human Th1/Th17 cells. The inhibition of TNFα and IL-6 by Compound A and the inhibition of IL-22, IL-17, and IL-8 by calcipotriol is maintained by the combination treatment.

Effect of Several PDE4 Inhibitors Alone or in Combination with Calcipotriol

Several PDE4 inhibitors in clinical development (Roflumilast, Tetomilast, GSK256066, Oglemilast, Apremilast and AN2728) have been tested for the effect on the activity of the human Th1/Th17 cells when given alone or in combination with calcipotriol.

Figure 5:
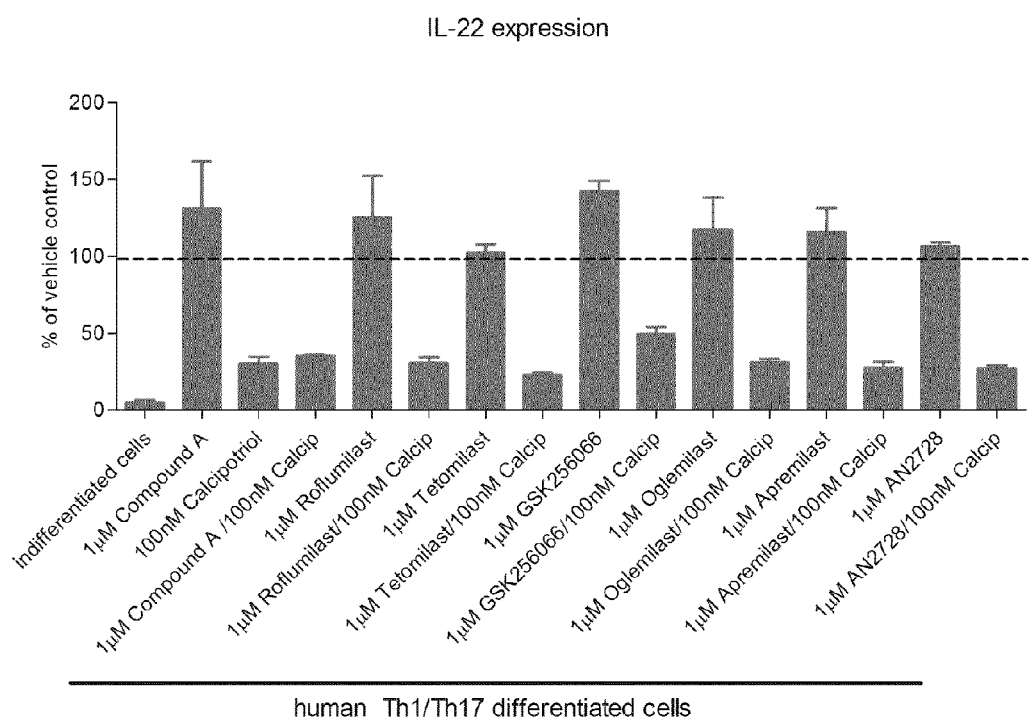
FIG. 5 is a graph showing the effect on the expression of IL-22 in Th1/Th17 cells of calcipotriol in a concentration of 100 nM and of seven different PDE4 inhibitors in a concentration of 1 μM alone or in combination. "Calcip" is calcipotriol.

As shown in FIG. 5, compared to vehicle treated control (represented by the dotted line) treatment with 100 nM of calcipotriol alone significantly inhibits the expression and secretion of IL-22 by human Th1/Th17 cells. On the contrary, compared to vehicle treated control, treatment with Compound A or all tested PDE4 inhibitors alone increases the expression of IL-22 by human Th1/Th17 cells.

Moreover, the treatment with a combination of PDE4 inhibitors and calcipotriol significantly inhibits the expression and secretion of IL-22 by human Th1/Th17, regardless of which PDE4 inhibitors is present in the combination. In other words, all PDE4 inhibitors in clinical development tested in this study (Roflumilast, Tetomilast, GSK256066, Oglemilast, Apremilast and AN2728) show comparable efficacy to Compound A and the upregulation of IL-22 expression mediated by the inhibition of PDE4 activity can be counteracted by calcipotriol.

Effect of Several Vitamin D Analogues Alone or in Combination with Compound a

Several vitamin D analogues in clinical use (calcipotriol, calcitriol, tacalcitol and maxacalcitol) have been tested for the effect on the activity of the human Th1/Th17 cells when given alone or in combination with Compound A.

Figure 6:
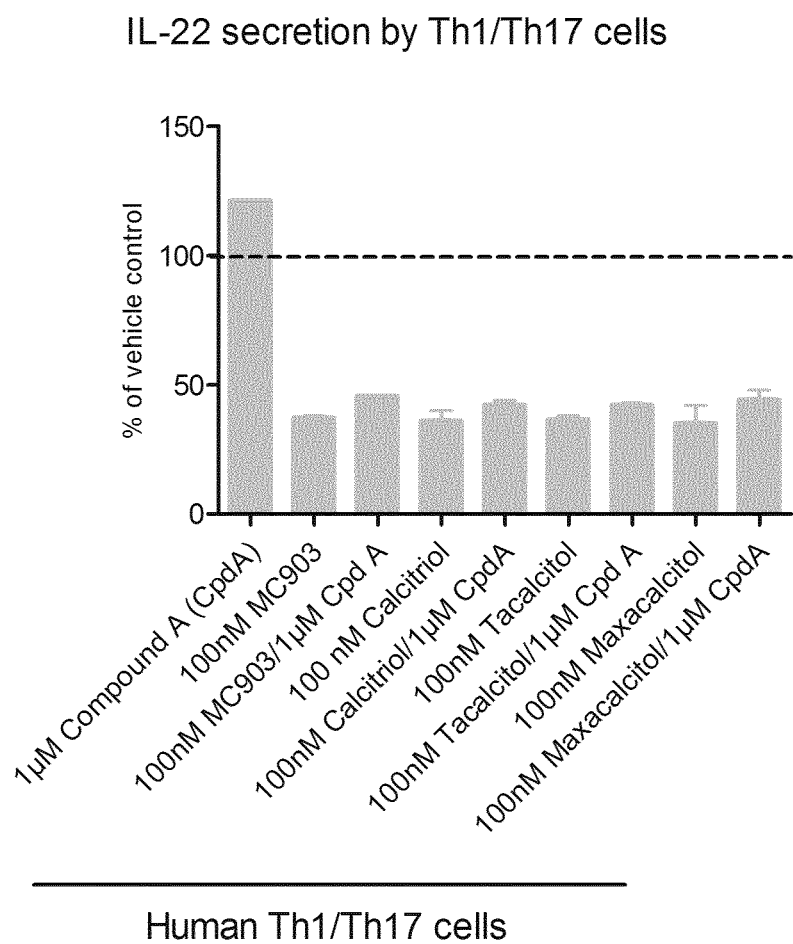
FIG. 6 is a graph showing the effect on the expression of IL-22 in Th1/Th17 cells of Compound A in a concentration of 1 μM alone or in combination with four different vitamin D analogues in a concentration of 100 nM.

As shown in FIG. 6, compared to vehicle treated control (represented by the dotted line) treatment with 100 nM of calcipotriol alone significantly inhibits the expression and secretion of IL-22 by human Th1/Th17 cells. Similarly, treatment with all tested vitamin D analogues alone (all tested at 100 nM) also significantly inhibits the expression and secretion of IL-22 by human Th1/Th17 cells and the effect is comparable to the one observed after treatment with 100 nM of calcipotriol.

On the contrary, compared to vehicle treated control, treatment with Compound A alone alone increases the expression of IL-22 by human Th1/Th17 cells.

Moreover, the treatment with a combination of Compound A and vitamin D analogues significantly inhibits the expression and secretion of IL-22 by human Th1/Th17, regardless of which vitamin D analogue is part of the combination. In other words, all vitamin D analogues in clinical use tested in this study (calcipotriol, calcitriol, tacalcitol and maxacalcitol) show comparable efficacy as Calcipotriol in counteracting the upregulation of IL-22 expression mediated by the inhibition of PDE4 activity.

Effect of Different Concentrations of Calcipotriol in the Presence and Absence of Compound A Different concetrations of calcipotriol (MC903) have been tested for effect on the activity of the human Th1/Th17 cells in the presence or absence of Compound A in a concentration of 1 µM. The purpose of the study was to identify the minimal concentration of calcipotriol needed to inhibit the upregulation of IL-22 expression mediated by the PDE4 inhibitor.

Figure 7:
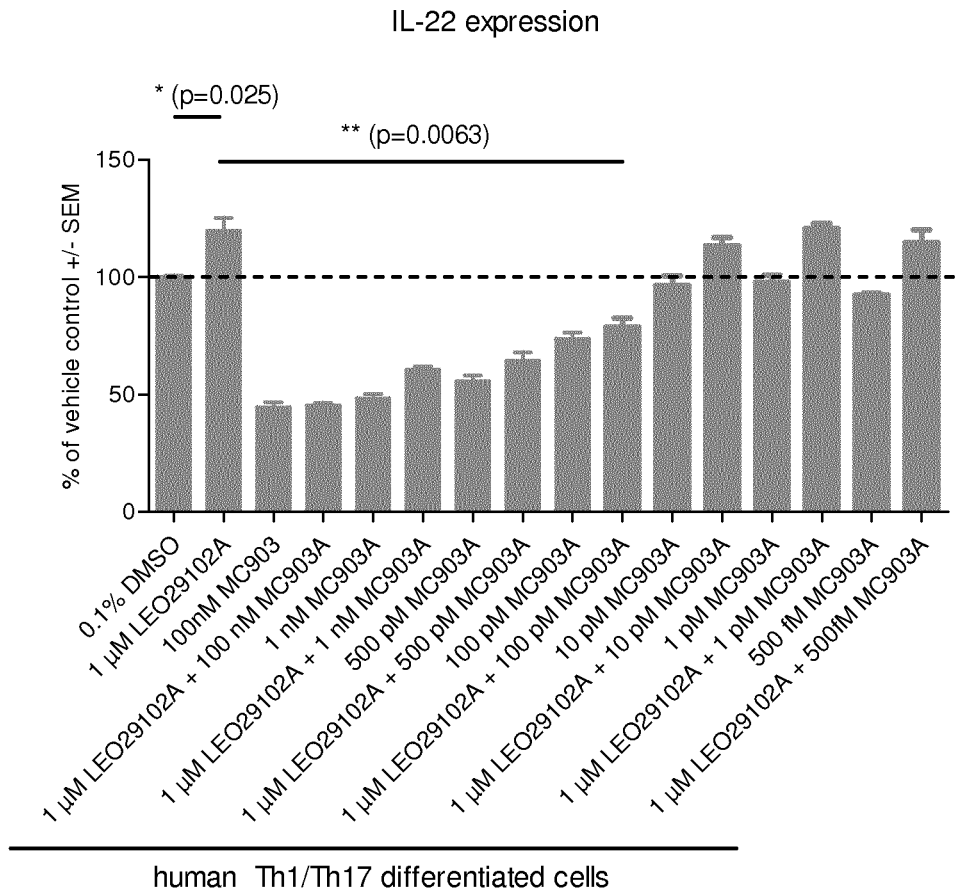
FIG. 7 is a graph showing the effect of different concentrations of calcipotriol (MC903) on the expression of IL-22 in Th1/Th17 cells in the presence or absence of Compound A in a concentration of 1 μM.

As shown in FIG. 7, compared to vehicle treated control (represented by the dotted line), treatment of with 100 nM of calcipotriol alone inhibits the expression and secretion of IL-22 by human Th1/Th17 cells whereas treatment with Compound A alone increases the expression of IL-22 by human Th1/Th17 cells.

Treatment with different concentrations of calcipotriol (100 nM, 1 nM, 500 pM and 100 pM) together with Compound A inhibited the upregulation of IL-22 expression. This effect was lost at a concentration of 10 pM of calcipotriol.

The results show that the effect of calcipotriol on IL-22 expression may be obtained at a much lower concentration than that required to affect keratinocyte proliferation (28 nM). This means that the combination of PDE4 inhibitor and vitamin D receptor agonist may be used in the treatment of conditions where an anti-inflammatory effect is needed without concomitantly affecting keratinocyte proliferation.

The invention claimed is:

1. A method for the treatment of an inflammatory skin disease or condition by inhibiting the upregulation of the expression of the proinflammatory cytokine interleukin-22 (IL-22) in activated and differentiated human T-cells, said upregulation being induced by administration of a therapeutically effective amount of a phosphodiesterase 4 (PDE4) inhibitor without concomitantly affecting keratinocyte proliferation, the method comprising administering to a patient in need thereof, either sequentially to or simultaneously with the administration of the PDE4 inhibitor, a vitamin D receptor agonist in an amount more than 1000 times lower than the amount of the PDE4 inhibitor so as to inhibit the upregulation of IL-22 expression and treat the inflammatory disease or condition;

wherein the vitamin D receptor agonist is selected from the group consisting of calcipotriol, calcitriol, tacalcitol and maxacalcitol;

wherein the PDE4 inhibitor is selected from the group consisting of roflumilast, GSK256066, oglemilast, tetomilast, apremilast, AN2728, 2-{6-[2-(2,3-dichloro-pyridin-4-yl)acetyl]-2,3-dimethoxyphenoxy}-N-propylacetamide (Compound A), N-benzyl-2-{6-[2-(3,5-dichloropyridin-4-yl)acetyl]-2,3-dimethoxyphenoxy}acetamide (Compound B), 2-(3,5-dichloropyridin-4-yl)1-{2-[2-(4-fluorophenyl)ethoxy]-3,4-dimethoxyphenyl}ethanone (Compound C), 2-(3,5-dichloropyridin-4-yl)-1-{9-methoxy-spiro[2H-1,5-benzodioxepin-3(4H),3'-oxetane]-6-yl}ethanone (Compound D), and 2-{6-[2-(3,5-dichloropyridin-4-yl)acetyl]-2,3-dimethoxyphenoxy}-N-(2-dimethylamino-ethyl)acetamide (Compound E); and wherein the inflammatory skin disease or condition is selected from psoriasis, epidermal inflammation, alopecia, skin atrophy, steroid induced skin atrophy, skin ageing, photo skin ageing, acne, dermatitis, atopic dermatitis, seborrheic dermatitis, contact dermatitis, urticaria, pruritus, and eczema.

2. The method of claim 1, wherein the vitamin D receptor agonist is calcipotriol or calcipotriol monohydrate.

3. The method of claim 1, wherein the PDE4 inhibitor is 2-{6-[2-(2,3-dichloropyridin-4-yl)acetyl]-2,3-dimethoxy-phenoxy}-N-propylacetamide (Compound A) or 2-(3,5-dichloropyridin-4-yl)-1-{9-methoxy-spiro[2H-1,5-benzodiox-epin-3(4H),3'-oxetane]-6-yl}ethanone (Compound D).

4. A pharmaceutical composition for use in the treatment of an inflammatory skin disease or condition which inhibits the upregulation of the expression of the proinflammatory cytokine interleukin-22 (IL-22) in activated and differentiated human T-cells, said upregulation being induced by administration of a therapeutically effective amount of a phosphodiesterase 4 (PDE4) inhibitor without concomitantly affecting keratinocyte proliferation, wherein the composition comprises a vitamin D receptor agonist in an amount more than 1000 times lower than the amount of the PDE4 inhibitor so as to inhibit the upregulation of IL-22 expression and treat the inflammatory disease or condition;

wherein the vitamin D receptor agonist is selected from the group consisting of calcipotriol, calcitriol, tacalcitol and maxacalcitol;

wherein the PDE4 inhibitor is selected from the group consisting of roflumilast, GSK256066, oglemilast, tetomilast, apremilast, AN2728, 2-{6-[2-(2,3-dichloro-pyridin-4-yl)acetyl]-2,3-dimethoxyphenoxy}-N-pro-pylacetamide (Compound A), N-benzyl-2-{6-[2-(3,5-dichloropyridin-4-yl)acetyl]-2,3-dimethoxyphenoxy}acetamide (Compound B), 2-(3,5-dichloropyridin-4-yl)1-{2-[2-(4-fluorophenyl)ethoxy]-3,4-dimethoxyphenyl}ethanone (Compound C), 2-(3,5-dichloropyridin-4-yl)-1-{9-methoxy-spiro[2H-1,5-benzodioxepin-3(4H),3'-oxetane]-6-yl}ethanone (Compound D), and 2-{6-[2-(3,5-dichloropyridin-4-yl)acetyl]-2,3-dimethoxyphenoxy}-N-(2-dimethylamino-ethyl)acetamide (Compound E); and wherein the inflammatory skin disease or condition is selected from psoriasis, epidermal inflammation, alopecia, skin atrophy, steroid induced skin atrophy, skin ageing, photo skin ageing, acne, dermatitis, atopic dermatitis, seborrheic dermatitis, contact dermatitis, urticaria, pruritus, and eczema.

5. The pharmaceutical composition of claim 4, wherein the vitamin D receptor agonist is calcipotriol or calcipotriol monohydrate.

6. The pharmaceutical composition of claim 4, wherein the PDE4 inhibitor is 2-{6-[2-(2,3-dichloropyridin-4-yl)acetyl]-2,3-dimethoxyphenoxy}-N-propylacetamide (Compound A) or 2-(3,5-dichloropyridin-4-yl)-{9-methoxy-spiro[2H-1,5-benzodioxepin-3(4H),3'-oxetane]-6-yl}ethanone (Compound D).

7. The pharmaceutical composition of claim 4, wherein the PDE4 inhibitor is present in an amount of from about 0.01 to 20% by weight, and the vitamin D receptor agonist is present in an amount of from about 0.0001 to 2.0% by weight.

8. The method of treatment of claim 4, wherein the PDE4 inhibitor is present in an amount of from about 0.01 to 20% by weight, and the vitamin D receptor agonist is present in an amount of from about 0.0001 to 2.0% by weight.

* * * * *